United States Patent [19]
Matta et al.

[11] Patent Number: 5,972,907
[45] Date of Patent: Oct. 26, 1999

[54] SYNTHETIC CORE 2-LIKE BRANCHED STRUCTURES CONTAINING GALNAC-LEWIS$^x$ AND NEU5AC$\alpha$2-3GAL$\beta$1-3GALNAC SEQUENCES AS NOVEL LIGANDS FOR SELECTINS

[75] Inventors: Khushi L. Matta, Williamsville, N.Y.; Rakesh K. Jain, Lawrenceville, N.J.

[73] Assignee: Health Research, Inc., Buffalo, N.Y.

[21] Appl. No.: 08/962,113

[22] Filed: Oct. 31, 1997

[51] Int. Cl.$^6$ ............... A61K 31/715; C07H 15/00
[52] U.S. Cl. ............... 514/54; 514/25; 536/4.1; 536/17.2; 536/17.5; 536/53; 536/54; 536/55; 536/55.1; 536/55.2; 536/117; 536/118; 536/119; 536/123.1
[58] Field of Search ............... 514/25, 54; 536/4.1, 536/17.2, 17.5, 53, 54, 55, 55.1, 55.2, 117, 118, 119, 123.1

Primary Examiner—Kathleen K. Fonda
Attorney, Agent, or Firm—Michael L. Dunn

[57] ABSTRACT

Compounds which bind to selectin receptors and thus may modulate the course of inflammation, cancer and related processes by intervening with cell-cell adhesion events. Further, such compounds can be used for identification and analysis of such receptors. In this regard the invention is directed to compounds of formula (I).

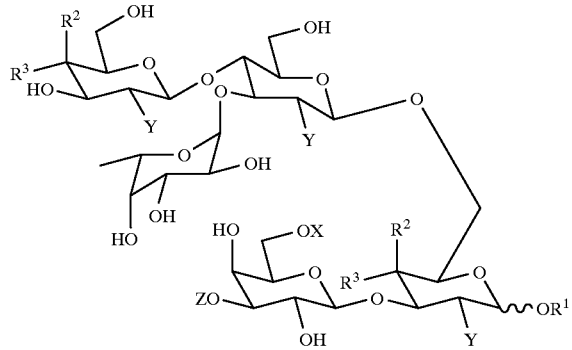

wherein $R^1$ is independently H, alkyl, aryl, an aryl alkyl, alkenyl or one or more additional saccharide residues; $R^2$=H or OH provided that when $R^2$ is H, $R^3$ is OH; $R^3$=H or OH provided that when $R^3$ is H, $R^2$ is OH; X=H, $SO_3^-$ or $PO_4^-$; Y is independently H, OH, $OR^4$ or $NHCOR^4$, wherein $R^4$ is alkyl, and Z is an organic acid residue. $\alpha$-L-Fucose residue can be modified or replaced with suitable bioisosters or a different saccharide residue such as D-mannose. Modification of L-fucose may include replacement of each or all of the hydroxyl groups with H or OR' wherein R' can be methyl, ethyl or allyl groups.

8 Claims, 9 Drawing Sheets

1. $R^1$ = OAc
2. $R^1$ = SPh

3.

4.

5.

6. $R^1$ = Bn; $R^2$ = $R^3$ = Ac

7.

8a.

9a. $R^1 = R^2 = R^3 = COCH_2C$; $R^4, R^4 = CHPhOMe$

9b. $R^1 = R^2 = R^3 = COCH_2Cl$; $R^4 = H$

10

11. R = OAc

12. R = SPh

15

| (i) Lithium iodide - pyridine
| (ii) Methanol - hydrazine hydrate/ 80°C
| (iii) MeOH - Et$_3$N - AC$_2$O
| (iv) NaOMe - MeOH (16)

18.

(i) SO₃ - pyridine -
N,N - DMF - 0°C
(ii) MeOH - Hydrazine hydrate
(iii) MeOH - Et₃N - AC₂O
(iv) NaOMe - MeOH

19.

SYNTHETIC CORE 2-LIKE BRANCHED STRUCTURES CONTAINING GALNAC-LEWIS$^x$ AND NEU5AC$\alpha$2-3GAL$\beta$1-3GALNAC SEQUENCES AS NOVEL LIGANDS FOR SELECTINS

TECHNICAL FIELD

The invention relates to compounds useful in the treatment of inflammation, allergic reactions, autoimmune diseases, cancer, and similar other conditions that are cell adhesion-dependent. More specifically, the invention concerns compounds, containing GalNAc lewis$^x$ as a mucin Core 2 branched structure, which have the ability to bind selectin receptors. Such structures have not been reported to be part of any O-linked glycoproteins. The invention is also concerned with pharmaceutical compositions containing such compounds. It is also directed to methods useful for the synthesis of such compounds and analogs derived therefrom.

BACKGROUND ART

It is now well established that cellular interactions are at least in part mediated by receptor/ligand interactions. An important class of receptors is a family of three calcium-dependent mammalian lectins, known as L, P and E-selectins, that have the ability to mediate the early steps of recruitment of leukocytes from blood stream in a variety of normal and pathologic situations. All three selectins recognize carbohydrate-based ligands such as sialyl lewis$^x$ (S Le$^x$), sialyl lewis$^a$, sulfated lewis$^x$ and sulfated lewis$^a$ type of structures. Several natural ligands of the selectins have been described, many of which share the biochemical properties of sialomucins. Recently, efforts have been directed towards the production of artificial selectin ligands, including compounds that mimic the sialyl lewis$^x$ structure. However, the affinity of selectins to such synthetic analogs was poor when compared to that of the natural glycoprotein ligands (such as GlyCAM-1, CD34), the mucosal addressin-cell adhesion molecule-1 (MadCAM-1), and an as yet unidentified 200 kDa glycoprotein ligand (Rosen, S. D. et al. Curr. Opin. Cell Biology 6:663–673 (1994)). Rosen and co-workers demonstrated that the O-glycans of GlyCAM-1 are sialylated, fucosylated and sulfated, and that all three components are important for binding. It is surprising that PSGL-1 from HL-60 cells is not heavily fucosylated, and a majority of O-glycans are disialylated or neutral forms of Core 2 structures. A monosialylated trifucosylated glycan with a polylactosamine backbone at the C-6 of GalNAc in the Gal$\beta$1→3GalNAc has also been reported as a minor constituent of PSGL-1.

In a recent study, it was observed that the compound NeuAc$\alpha$2→3SE-6 Gal$\beta$1→4(Fuc$\alpha$1→3)GlcNAcOMe, which is pall of GlyCAM-1, was not a superior ligand for L-selectin. Both this compound and NeuAc$\alpha$2→3Gal$\beta$1→4(Fuc$\alpha$1→3)SE-3GlcNAc$\beta$1→3Gal, which was used by Scudder and co-workers in inhibition studies (Scudder, P. R., et al., Glycobiol. 44:929→933 (1994)), lacked a high affinity for L-selectin. As mentioned earlier, many of the natural ligands are sialomucin type (or O-linked glycans). However, an extended trimannosyl oligosaccharide (N-linked type glycan) containing GalNAc Le$^x$ [GalNAc$\beta$1→4(Fuc$\alpha$1→3)GlcNAc$\beta$1→Man$\alpha$1→⅗Man$\beta$1→4GlcNAc$\beta$1→4GlcNAc] was isolated from human cell produced Protein C, and shown to be a potent inhibitor for E-selectin.

Several theories have been postulated to explain the disparity between the high affinities of the selectins for their natural ligands and the relatively poor affinities for the sialylated/sulfated fucosylated lactosamines. Simple multivalency of both oligosaccharide and selectin on intact cell surfaces or by presentation on a polypeptide backbone could enhance avidity. This is apparent from comparison studies of the IC$_{50}$ of monomeric, dimeric and tetravalent forms of SLe$^x$ for E-selectin, with the latter showing considerable improvement in inhibiting L-selectin. Nonetheless, P- and L-selectins do not bind to some cell types that express considerable amounts of SLe$^x$, and cell recognition is usually destroyed by mucin-degrading enzyme O-sialoglycoprotease, even when the vast majority of cell surface SLe$^x$ remains intact after this treatment, indicating the insufficiency of simple ligand multivalency for explaining biologically relevant selectin binding. Multivalent aggregation of selectins could also be invoked. However, the high affinity binding of soluble monomeric E- and P-selectin to cell surfaces, indicates that this is not essential. Moreover, there is no published evidence thus far for naturally occurring multimerization of selecting. Similarly, the possibility of multiple binding sites within a single selectin lectin domain is unlikely, based on studies which indicate that the binding sites for carbohydrates are quite small. Alternatively, it could be hypothesized that the natural selectin ligands carry rare structural variants of the common sialylated fucosylated oligosaccharides which are responsible for the high affinity interaction. Because of the role of selectins in disease, particularly diseases involving undesired cell-cell adhesion that occurs through selectin-ligand binding on defined cell types, the identification and procurement of novel ligands that would allow the regulation of this type of selectin-ligand binding is greatly needed.

BRIEF DESCRIPTION OF THE INVENTION

The invention provides compounds which bind to selectin receptors and thus may modulate the course of inflammation, cancer and related processes by intervening with cell-cell adhesion events. Further, such compounds can be used for identification and analysis of such receptors. In this regard the invention is directed to compounds of formula (I).

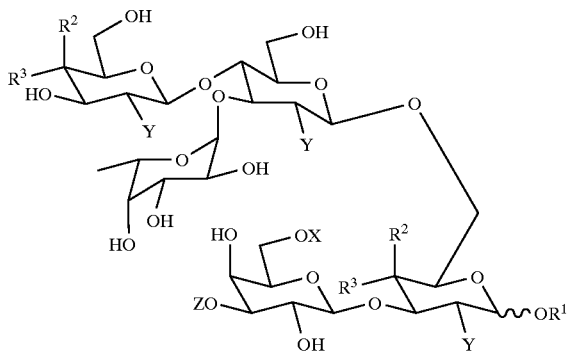

wherein $R^1$ is independently H alkyl, aryl, an aryl alkyl, alkenyl or one or more additional saccharide residues;

$R^2$=H or OH provided that when $R^2$ is H, $R^3$ is —OH;
$R^3$=H or OH provided that when $R^3$ is H, $R^2$ is —OH;
X=H, $SO_3^-$ or $PO_4^-$;
Y is independently H, OH, $OR^4$ or $NHCOR^4$, wherein $R^4$ is alkyl, and
Z is an organic acid residue.

α-L-Fucose residue can be modified or replaced with suitable bioisosteres or a different saccharide residue such as D-mannose. Modification of L-fucose may include replacement of each or all of the hydroxyl groups with H or OR' wherein R' can be methyl, ethyl or allyl groups.

Figure 1:
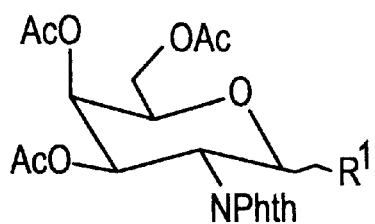
FIG. 1 shows the structural formulas of glycosyl donors and acceptors employed for synthesis of compounds 16 and 19 of the invention.
Figure 1:
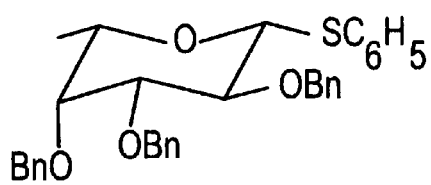
Figure 1:
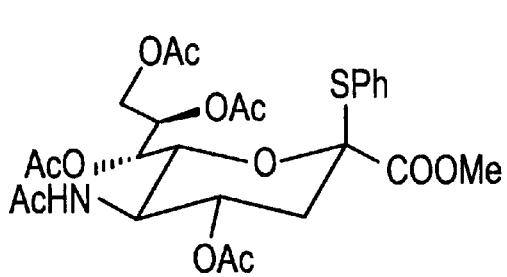
Figure 1:
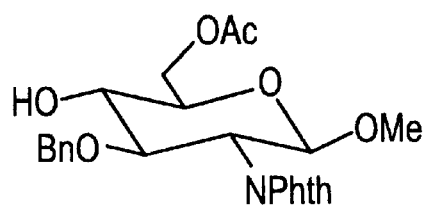
Figure 2:
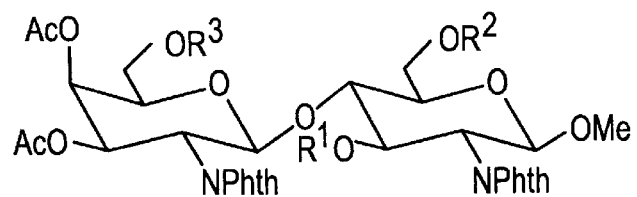
FIG. 2 shows the structural formulas of glycosyl donors and acceptors employed for synthesis of compounds 16 and 19 of the invention.
Figure 2:
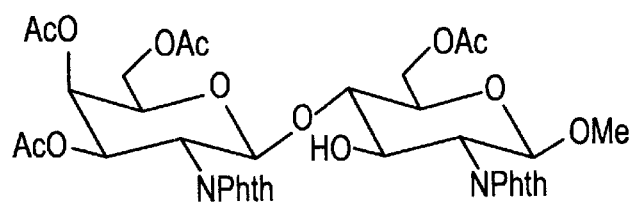
Figure 2:
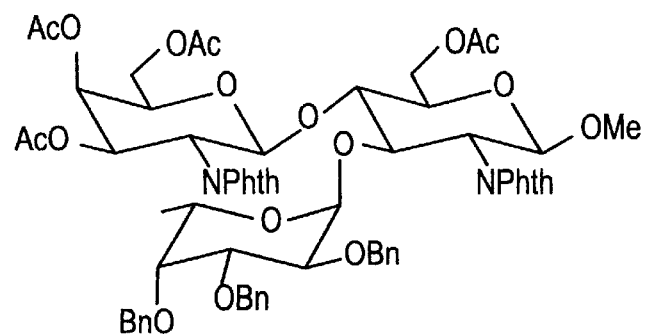
Figure 3:
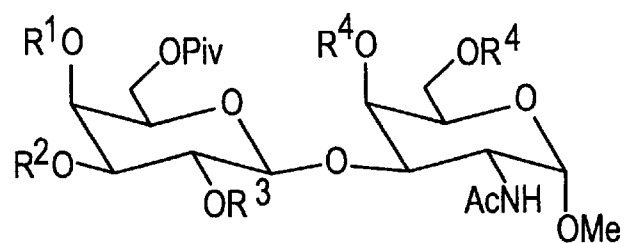
FIG. 3 shows the structural formulas of glycosyl donors and acceptors employed for synthesis of compounds 16 and 19 of the invention.
Figure 3:
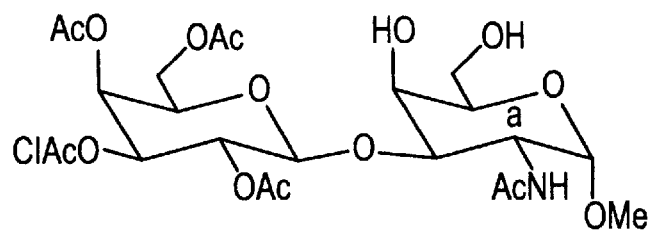
Figure 3:
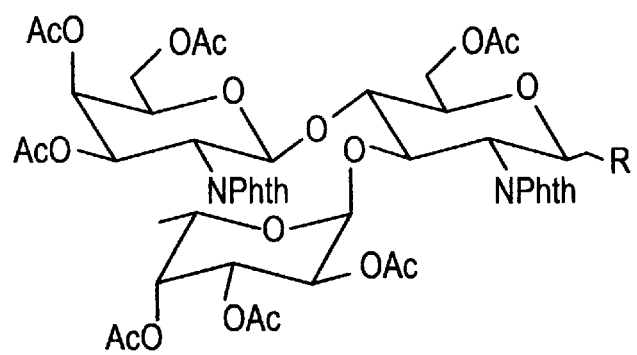
Figure 4:
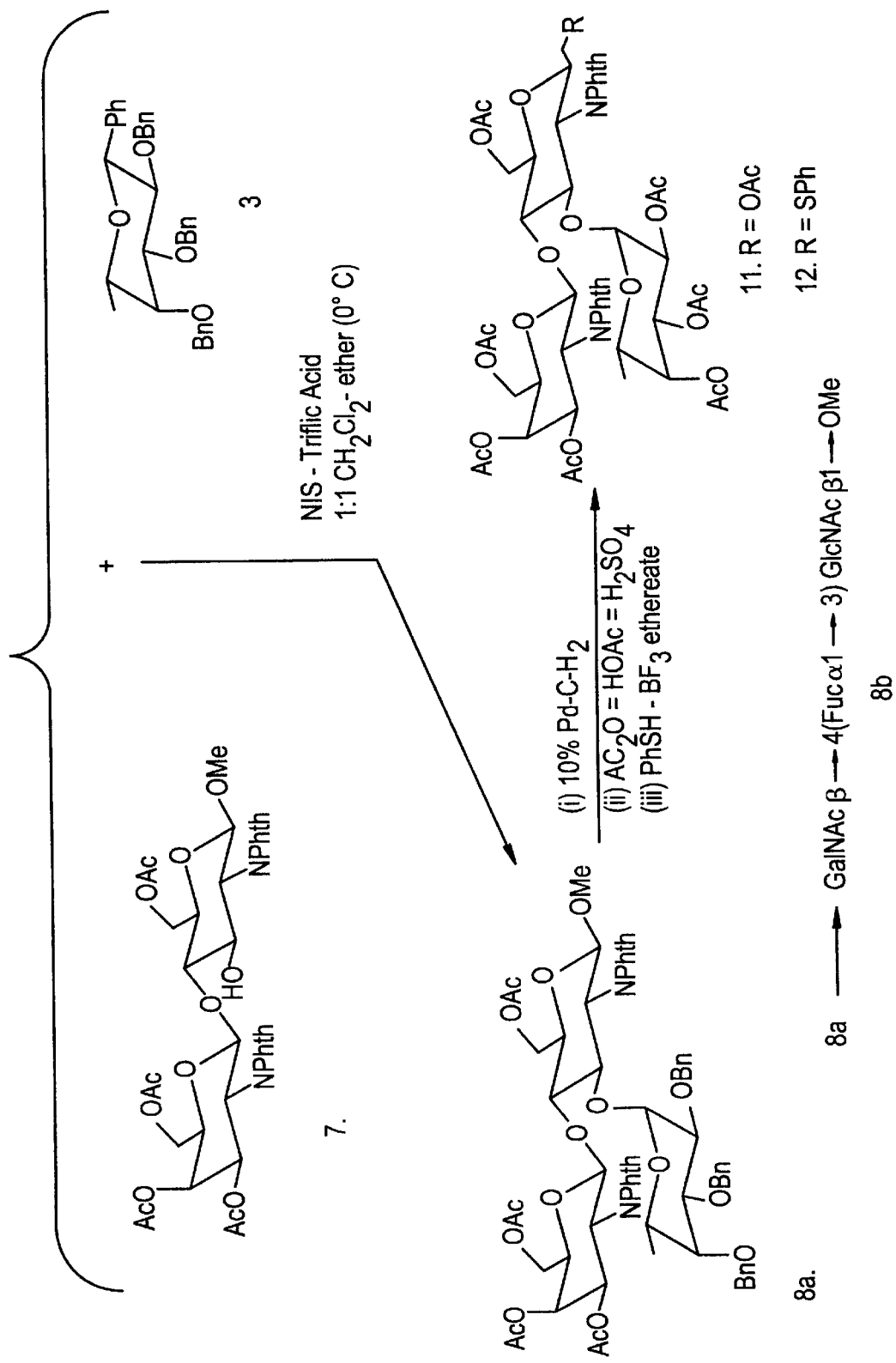
FIG. 4 shows a schematic diagram of a reaction for preparation of compounds 11 and 12.
Figure 5:
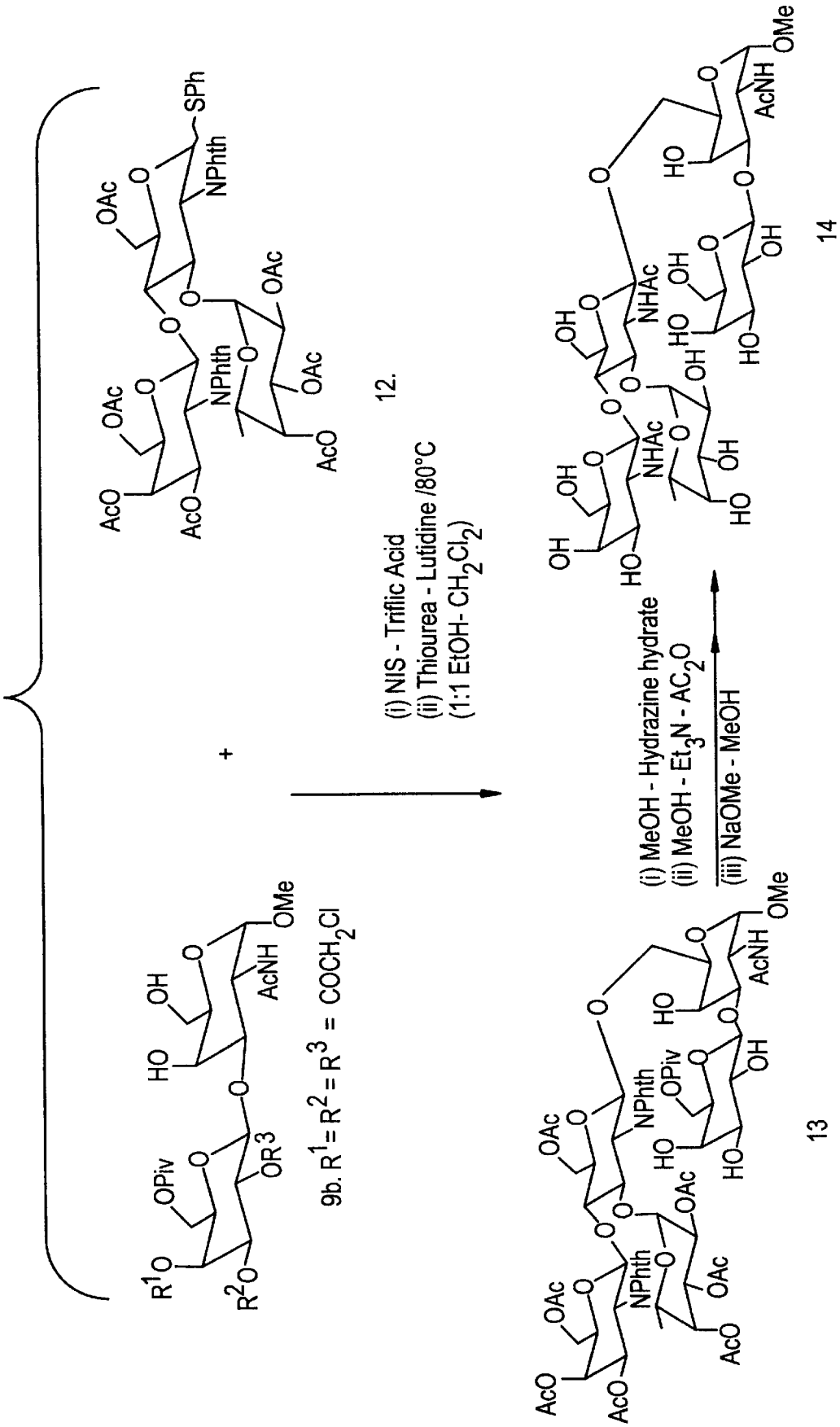
FIG. 5 shows a schematic diagram of a reaction for preparation of compound 14.
Figure 6:
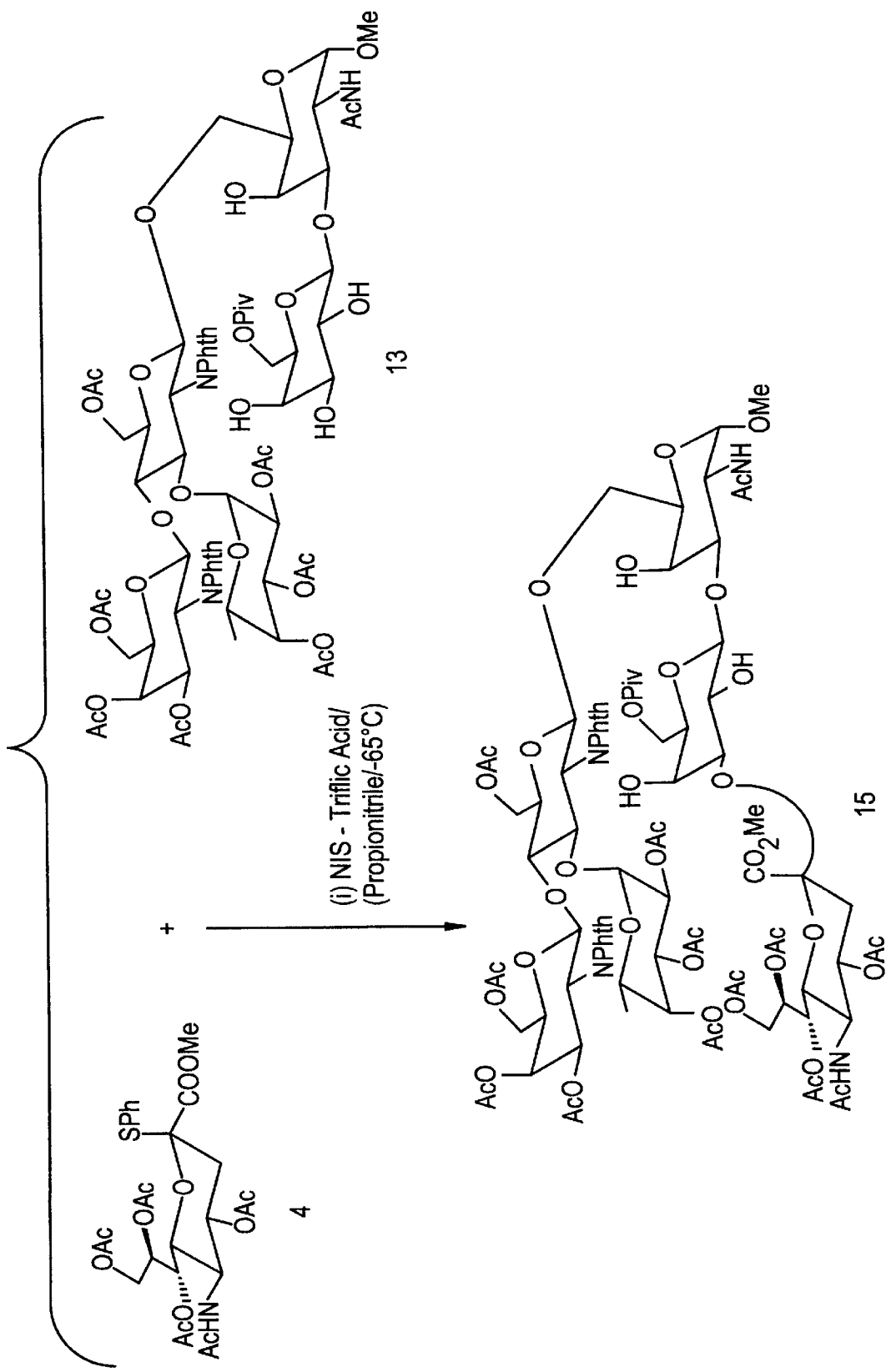
FIG. 6 shows a schematic diagram of a reaction for preparation of compound 15.
Figure 7:
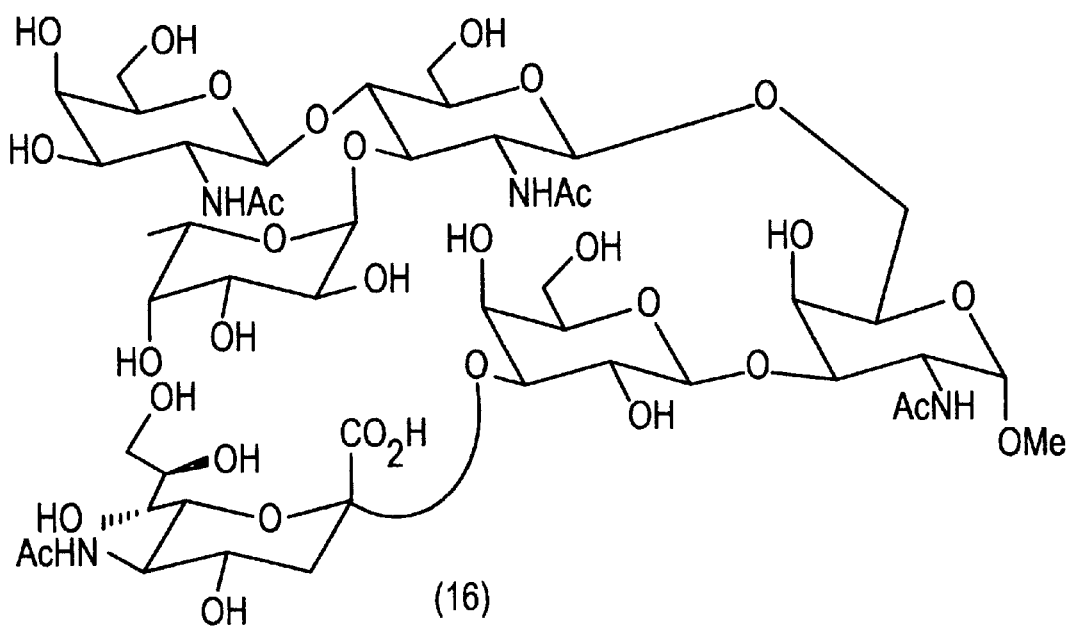
FIG. 7 shows a schematic diagram of a reaction for preparation of compound 16.
Figure 8:
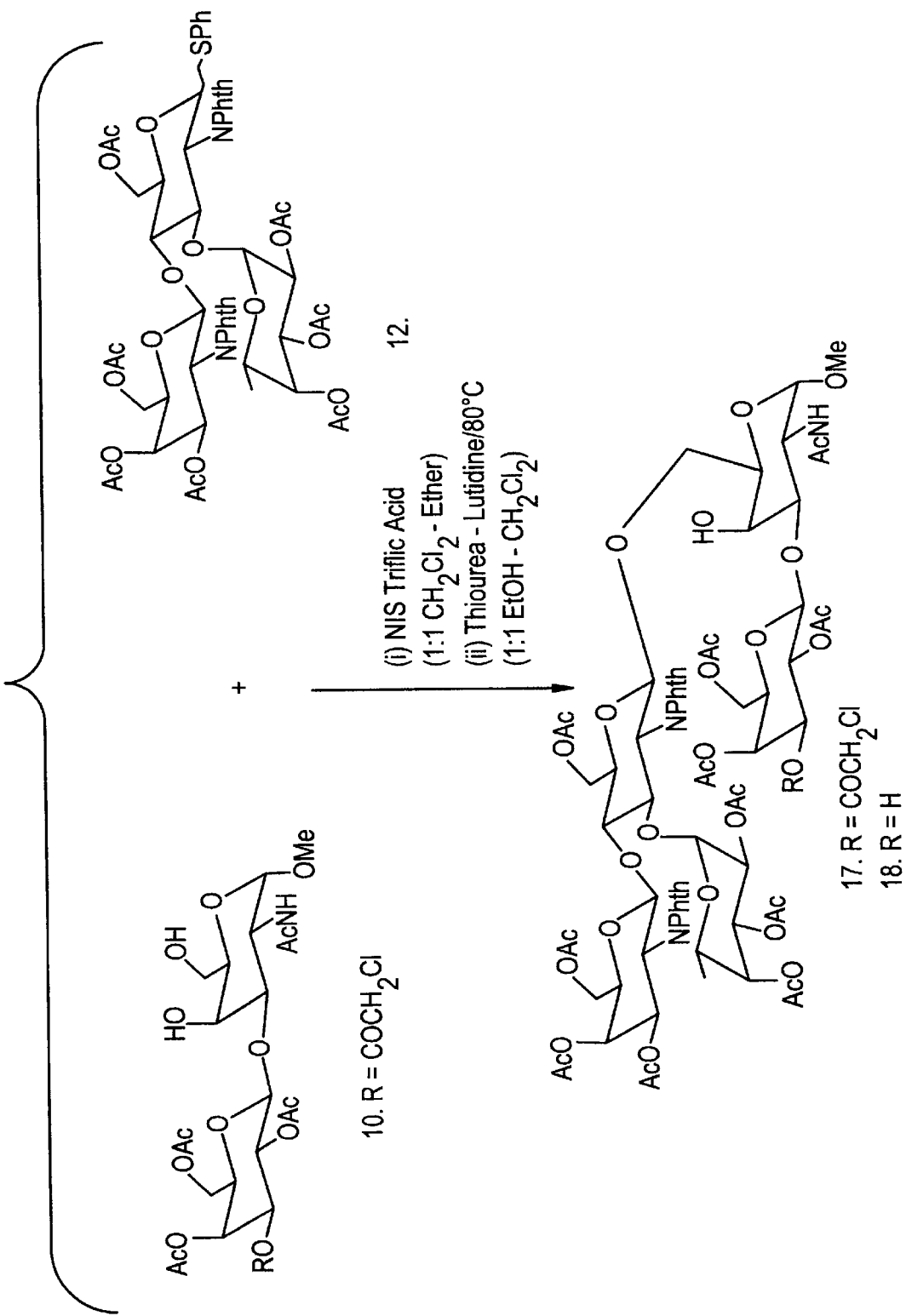
FIG. 8 shows a schematic diagram of a reaction for preparation of compounds 17 and 18.
Figure 9:
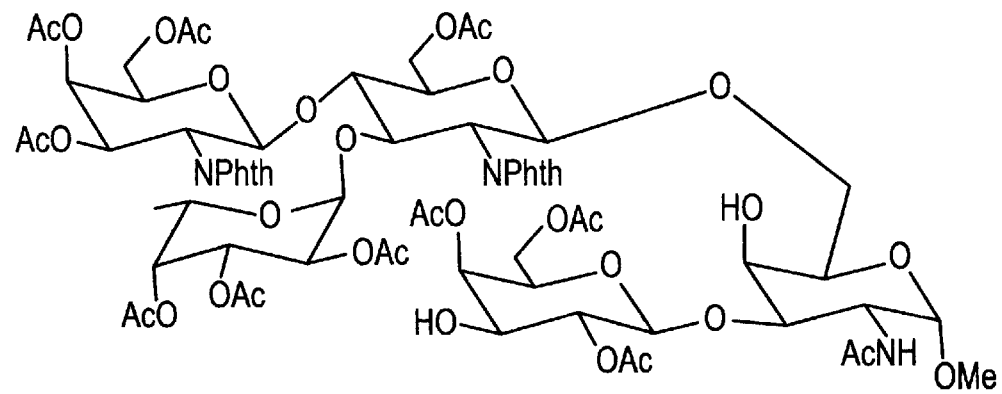
FIG. 9 shows a schematic diagram of a reaction for preparation of compound 19.
Figure 9:
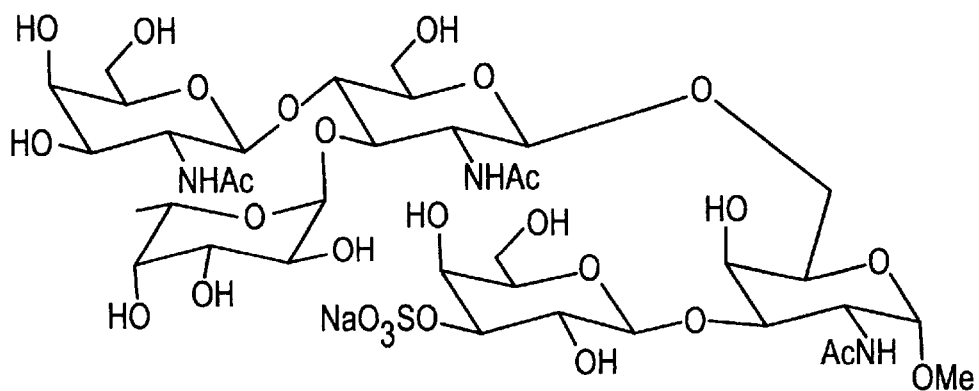

In another aspect, the invention is directed to a method to synthesize said compound of formula (1) and derivatives, which method comprises employing various standard and novel litermediates, for example, such as those depicted herein below (see FIGS. 1–3). Such intermediates are not limited to the examples given and may vary, depending on the nature of the final product desired. Such intermediates are used in a convergent or a stepwise manner to procure the final fully or partially-protected compounds for example (13 and 15) which would produce the desired selectin inhibitors (14) or (16) on systematic removal of the protecting groups by procedures well known in the art. Similarly, intermediate (17) can be selectively de-O-chloroacylated to give (18) which is converted into the desired sulfated inhibitor (19) by way of a partially protected intermediate.

DETAILED DESCRIPTION OF THE INVENTION

"alkenyl" includes substituted and unsubstituted alkenyl. "alkyl" as used herein included substituted and unsubstituted alkyl groups of up to 22 carbon atoms. The alkyl group is preferably lower alkyl of one through four carbon atoms or higher alkyl of 5 through 15 carbon atoms.

"aryl" includes substituted and unsubstituted alyl groups.

"organic acid residue" means carboxylic acids and carboxylic acid esters including substituted and unsubstituted carboxylic acids such as amine acids, sialic acid, N-acetyl neuraminic acid, acetic acid and propionic acid and other organic acid groups sharing the general formula (—$CH_2$) COOH, where r is 1–8.

"substituted" as used herein means substituted with one or more hydroxy, carboxy, amino, sulfo, chloro, ester, ether, or thioether groups. It is to be understood that such substitution groups may themselves be substituted.

This invention provides compounds that can be used in the treatment of inflammation by virtue of their ability to bind to selectin receptors (for review see ref. 8). For example, when a tissue is infected, it defensively secretes cytokines, such as interleukin-1 and tumor necrosis factor. The cytokines stimulate endothelial cells in the venules to express P- and E-selectins on their surfaces. White blood cells circulating in the blood vessels contain on their surfaces carbohydrate ligands capable of binding to these selectins. Once attached to a wall of a venule, a leukocyte can leave the blood stream by squeezing between the adjacent endothelial cells and into the surrounding tissue. This process is essential for the infection-fighting role of the leukocytes. Yet acting inappropriately, this same process allows leukocytes to accumulate in tissues, thereby causing tissue damage, swelling and pain. The inflammation of rheumatoid arthritis, for instance, occurs when the white blood cells enter the joints and release protein-degrading enzymes, oxygen radicals and other toxic factors. Another example is reperfusion injury, a disorder that occurs after the flow of blood is temporarily cut off from a tissue, such as during a heart attack. When the blood resumes, the white blood cells destroy tissues damaged by lack of oxygen. A further use of compounds of formula 1 can be for treatment of septic shock.

The spread of cancer cells from the main tumor to other sites in the body occurs by a process known as metastasis. For metastasis to take place, cancer cells must migrate from their site of origin to the new site for colonization. It appears that malignant cells can recruit adhesion molecules in order to facilitate such migration. For example, adhesion of human colon tumor cells to endothelium has been shown to be mediated by E-selectin, and it has been suggested that sialyl lewis$^x$ and sialyl lewis$^a$ structures present on human colon cell surfaces are the ligands for E-selectin. Furthermore, an increased expression of dimeric sialyl lewis$^x$ antigen in metastatic cancers has been reported. Dimeric sialyl Le$^x$ structures are known to be selectin ligands. It is thus apparent that one way of combating metastasis is to interrupt this adhesion process. The compounds of the invention can act as anti-adhesive drugs and thus retard the spread of cancer cells which contain receptors that adhere to compounds of general formula (1), for example compounds 14, 16 and 19.

Nontherapeutic Uses of Compounds of Formula 1

The usefulness of compounds of formula 1 is not limited to treating or preventing cell-adhesion related conditions such as inflammation. They can also be employed in diagnostic and purification procedures.

Compounds of formula 1 may be attached to a solid support and used in affinity chromatography to purify selectin receptor proteins from biological samples. Compounds of formula 1 are able to adhere to such receptors in preference to other biological contaminants which can be washed off the affinity column leaving the desired protein to be subsequently eluted by adjusting the eluent in a manner that allows their release from the adsorbant, for example by adjusting the pH. Optimal conditions can readily be achieved by those familiar with affinity chromatography.

Compounds of formula 1 can also be used to detect the presence or absence of selectin or related carbohydrate-binding receptor ligands by virtue of their ability to complex with such receptor proteins. The amount of complex can be measured using various techniques. In some instances, it might be useful to employ compounds of formula 1 in labelled form, e.g., labeled with an isotope or a fluorescent structure, to allow for detection.

When coupled to suitable carriers, compounds of formula 1 can be used as immunogens to raise antibodies against them. The resulting antibodies will be useful in assays to determine the presence and/or the amount of the relevant compounds. By using such assays, it is possible to monitor the levels of compounds of formula (1) when they are used as therapeutic agents.

Additionally, compounds of formula 1, devoid of sialic acid residue and sulfate group (for example compound 14) can act as acceptor substrates for sialyl transferase and sulfotransferase enzymes. Thus, such compounds can also be utilized as intermediates for enzymatic synthesis of compounds of this invention.

Formulation and Administration

Compounds of the invention may be administered to a subject in need, for example, of preventing or relieving inflammation and/or the symptoms associated with it. The compounds are preferably administered with a pharmaceutically acceptable carrier, the nature of which differs with the mode of administration, i.e., whether it is oral, by injection or by the use of suppositories or in the form of topical application or nasal spray. Methods of preparing dosage forms are known to those skilled in the art (for example, see Remington's Pharmaceutical Sciences, Latest edition).

While the dosage may vary in amount according to the condition or subject, it is noteworthy that complete blocking of all selectin receptors of a particular type may not be desirable. Normal healing processes require that some white blood cells should reach the tissue afflicted with wound, infection or disease.

Compounds of formula 1 may be useful for treating a range of autoimmune diseases such as rheumatoid arthritis and multiple sclerosis by interfering with the tendency of the immune system to act against the body by recruiting white blood cells and inducing them to accumulate in the tissues thus causing tissue damage, swelling, inflammation and pain.

During heart attack, thrombolytic agents such as tissue plasminogen activator or streptokinase are used to relieve coronary obstruction in many patients. However, a number of these patients suffer what is known as reperfusion injury. Reperfusion injury is believed to be associated with adherence of leukocytes to vascular endothelium in the area with deficient blood flow (ischemic zone) (Romson et al., *Circulation* 67:1016–1023, 1983). The adherent leukocytes are then able to migrate to the ischemic myocardium and attack tissues which suffered damage during blood flow restriction and the accompanying lack of oxygen. Thus, by interfering with leukocyte adhesion in ischemic myocardium, compounds of formula (1) may greatly enhance the therapeutic value of thrombolytic agents and thus enhance the likelihood of the survival of heart attack patients.

Organ injury as a result of ischemia and reperfusion is also common in other clinical situations such as stroke, organ transplantation, etc. Administration of compounds for formula (1) may also be useful in such clinical disorders.

Multivalent Forms of Compounds of Formula (1)

The affinity of the compounds of the invention for binding with receptors can be enhanced by providing multiple forms of such compounds with optimal spatial arrangement of the presumed binding sites. For example, a considerable increase in binding with E- and L-selectins was observed when dimeric and tetrameric structures of SLe$^x$ were compared to the monomeric form. Multivalent structures of compounds of formula (1) can be obtained by attaching them to suitable scaffolds with multifinctional groups. This can be made possible by the choice of the aglycon. A free hydroxyl group at the reducing end would permit reductive amination with coupling to suitable peptides or proteins. Similarly, oxidation can result in carboxy groups, which, on reaction with amino or hydroxyl groups will result in amides or esters, respectively. Suitable aglycons that would allow subsequent polymerization can also be utilized.

Preparation of Compounds of formulas 14, 16 and 19

Appropriately protected glycosyl donors and acceptors can be utilized for the preparation of compounds of the general formula (1), and the choice of each will depend on the target compound to be prepared. For example, the glycosyl donors and acceptors (FIGS. 1–3) were employed for the synthesis of compounds of formulas (16) and (19) as illustrated in Schemes I–IV. A key glycosyl donor was phenyl 3,4,6-tri-O-acetyl-2-deoxy-2-phthalimido-1-thio-α/β-D-galactopyranoside (2). Compound 2 was prepared by treatment of known 1,3,4,6-tetra-O-acetyl-2-deoxy-2-phthalimido-α/β-D-galactopyranose (1) with thiophenol in dichloromethane and in the presence of borontlifluoride-ethearate. Compound (2) existed largely as the β-anomer (α/β ratio 1:4) as judged by its $^1$H NMR spectrum.

Regioselective acylation of methyl 3-O-benzyl-2-deoxy-2-phthalimido-β-D-glucopyranoside with acetyl chloride in pyridine afforded the 6-O-acetyl derivative (5) in 79% yield. Glycosylation (catalyzed by N-iodosuccinimide-triflic acid of 5 with donor 2 gave (6) in 52% yield. Hydrogenolytic cleavage of the benzyl group of 6 in glacial acetic acid and in the presence of 10% palladium-on-carbon furnished the partially protected disaccharide (7). α-L-Fucosylation of 7 with the tri-O-benzyl thiophenyl donor (3) in the presence of N-iodosuccinimide-triflic acid (Scheme I) afforded the fully-protected trisaccharide derivative (8) in 68% yield. Compound 8 was converted, in 76% yield, into the diphthaloyl peracetate (11) by hydrogenolysis (glacial acetic acid-10% Pd-C), followed by acetolysis (acetic anhydride-acetic-acid-sulfuric acid). Compound 11 was, in turn, converted (49% yield) into the key glycosyl donor (12) by treatment with thiophenol and boron-trifluoride ethearate.

Selective deacylation of methyl O-(2,3,4-tri-O-acetyl-6-O-trimethylacetyl-β-D-galactopyranosyl)-(1→3)-2-acetamido-2-deoxy-4,6-O-(4-methoxybenzylidene)-α-D-galactopyranoside (9a) in 1:1 dichloromethane-methanol (0.5 M NaOMe, pH ≠11), followed by chloroac;etylation and cleavage of the 4-methoxybenzylidene acetal with 70% aqueous acetic acid afforded compound 9b which was used in the next step.

N-Iodosuccinimide-triflic acid glycosylation of compound (9b) with glycosyl donor 12 (Scheme II), followed by removal of the chloroacetyl groups in the β-galactopyranosyl residue afforded the partially-protected pentasaccharide intermediate (13) in 35% yield (based on 12). The 1H NMR spectrum of 13 was in conformity with the overall structure expected (see Examples).

A similar glycosylation of compound (10) with 12 gave, in 76% yield, the pentasaccharide derivative (17), the chloroacetyl group of which was removed to give, in 71% yield, intermediate (18); Scheme IV. Compounds 13 and 18 are key intermediates for obtaining the desired inhibitors 14, 16 and 19. Thus, for the production of compound 14 the partially-protected 13 was subjected to complete removal of the blocking groups in three successive steps (see Example 9), whereas for obtaining the sialylated compound 16, the same intermediate 13 was allowed to react with known sialyl donor (4) to give, in 47% yield, the hexasacchalide derivative (15); (Scheme III). The α-configuration for the sialic acid residue was confirmed by the $^1$H NMR of 15 which exhibited a double doublet at δ2.67 (J=4.6 Hz), attributable to H-3e of this residue. The conversion of 15 into the target compound (16) (Scheme III) was performed in four successive steps: (1) lithium iodide-pyridine (methyl ester to free acid), (2) methanol-hydrazine hydrate (removal of the phthalimido group), (3) acetic anhydride-methanol-dichloromethane (N-acetylation), and (4) methanolic sodium methoxide (O-deacetylation). The $^1$H and $^{13}$C NMR spectra of 16 were in accord with the structure assigned (see Examples).

For the production of the target compound (19), intermediate 18 was treated with five molar equivalents of sulfur trioxide-pyridine complex in N,N-dimethylformamide at 0° C. (Scheme IV), followed by customary removal of the protecting groups. Column chromatographic purification on silica gel then farnished the desired compound 19 in 37% yield. The $^{13}$C NMR spectrum of 19 was also consistent with the structure assigned (see Examples).

EXAMPLES

General methods.—Optical rotations were measured at ≠25° C. with a Perkin-Elmer 241 Polarimeter. Thin layer chromatography (TLC) was conducted on glass plates pre-coated with 0.25 mm layers of silica gel 60F-254 (Analtech GHLF uniplates). The compounds were located by exposure u.v. light or by spraying with 5% $H_2SO_4$ in ethanol and charring, or by both techniques. The silica gel used for column chromatography was Baker Analyzed (60–200 mesh). NMR spectra were recorded at ≠25° C., $^1$H-spectra with a Varian EM-390 at 90 MHz and with a Bruker AM-400 at 400 MHz, and the $^{13}$C-spectra with a Bruker AM-400 at 100.6 MHz. All chemical shifts are referenced to tetramethylsilane. Solutions in organic solvents were generally dried with anhydrous sodium sulfate. Dichloromethane, N,N-dimethylformamide, 1,2-dichloroethane, benzene and 2,2-dimethoxypropane were kept dried over 4A° molecular sieves. Elemental analyses were performed by Robertson Laboratory, Madison, N.J., USA.

General procedure for glycosidation.—A solution of the acceptor (1.0–1.2 mmol) and donor (1.0–1.5 mmol) and N-iodosuccinimide (2.5–3.0 mmol) in dichloromethane (20 ml, for compound 6), 13 from 9b and 12, 17 or 1:1 dichloromethane-ether (30 ml, for compound 8 and 17), propionitrile (15 ml, for compound 15) was stirred for 0.5 h with 4 Å molecular sieves (2 g) under an argon atmosphere at 0° C. (compound 6 and 8), or –40° C. (compound 13 and 17) or –65° C. (compound 15). Then a dilute solution of trifluoromethanesulfonic acid (triflic acid, 0.2 ml in 10 ml dichloromethane or propionitrile) was added dropwise. Stirring was continued at the same temperature for an additional hour, and the acid was neutralized with aqueous sodium bicarbonate solution. The mixture was filtered (Celite bed), the solids thoroughly washed with water, saturated sodium bicarbonate solution, 10% sodium thiosulfate solution, dried and concentrated under diminished pressure.

The following examples are intended to illustrate but not to limit the invention.

Example 1

Preparation of phenyl 3,4,6-tri-O-acetyl-2-deoxy-2-phthalimido-1-thio-α/β-D-glucopyranoside (2).—To a stirred solution of 1 (6.4 g, 13.4 mmol) in dichloromethane (70 ml) was added thiophenol (4.0 ml, 36.4 mmol) and $BF_3$·ethereate (4.0 ml, 28.4 mmol). Stirring was continued for 4 h at room temperature. The reaction mixture was then washed with aqueous sodium bicarbonate solution, water, dried and concentrated. The residue was purified on a column of silica gel with a solvent gradient consisting of hexane-ethyl acetate 3:2→1:1 (v/v) to afford 2 (6.1 g, 84%); $[\alpha]_D$+28° (c 1.0, CHCl$_3$); $^1$H NMR (CDCl$_2$): δ7.88–7.26 (m, 9 H, arom.), 5.79 (dd, J=9.1 Hz and 10.1 Hz, 1 H, H-3), 5.70 (d, J=10.5 Hz, 0.8 H, H-1), 5.49 (d, J=3.5 Hz, 1 H, H-4), 2.2, 2.06 and 1.98 (each s, 3×OAc-α), 2.18, 2.04 and 1.81 (each s, 3×OAc-β).

Anal Calc. for $C_{26}H_{25}NO_9S$: C, 59.19; H, 4.78; N, 2.66. Found: C, 59.21; H, 4.91; N, 2.54.

Example 2

Preparation of 6-O-acetyl-3-O-benzyl-2-deoxy-2-phthalimido-β-D-glucopyranoside (5).—To a cold (–30° C.), stilled solution of methyl 3-O-benzyl-2-deoxy-2-phthalimido-β-D-glucopyranoside$^{54}$ (4.8 g, 11.6 mmol) in pyridine (50 ml) was added, dropwise, a solution of acetyl chloride (0.97 ml, 12.4 mmol) in pyridine-dichloromethane (1:2, 15 ml). Stirring was continued for 2 h at the same temperature, and then the mixture was kept overnight at 5°–6° C. It was then cooled to 0° C. and methanol (5 ml) was added to decompose excess reagent. The solvents were removed under diminished pressure and the residue dissolved in dichloromethane. The organic layer was successively washed with 10% aqueous hydrochloric acid, water, saturated sodium bicarbonate solution, dried and concentrated. The crude product was purified on a column of silica gel with a solvent gradient consisting of 40–50% ethyl acetate in hexane to give 5 (4.2 g, 79%); $[\alpha]_D$+23° (c 1.0, CHCl$_3$); $^1$H NMR (CDCl$_2$): δ7.73–6.98 (m, 9 H, arom.), 5.04 (dd, J=8.3 Hz, 1 H, H-1), 4.04 (dd, J=8.6 Hz, H-6), 3.37 (s, 3 H-OMe), 2.14 (s, 3 H, OAc).

Anal Calc. for $C_{24}H_{25}NO_8$: C, 63.29; H, 5.53; N, 3.08. Found: C, 63.31; H, 5.60; N, 3.01.

Example 3

Preparation of methyl O-(3,4,6-tri-O-acetyl-2-deoxy-2-phthalimido-β-D-galactopyranosyl)-(1→4)-6-O-acetyl-3-O-benzyl-2-deoxy-2-phthalimido-β-D-glucopyranoside (6).—Glycosidation of 5 (4.0 g, 8.6 mmol) with 2 (6.0 g, 11.1 mmol) followed by silica gel column chromatography (solvent gradient consisting of hexane-ethyl acetate 3:2→1:1) afforded 6 (6.1 g, 52%); $[\alpha]_D$+10° (c 1.0, CHCl$_3$); $^1$H NMR (CDCl$_2$): δ7.90–6.92 (m, 13 H, arom.), 5.79 (dd, 1 H, H-3'), 5.48 (d, J=8.7 Hz, 1 H, H-1), 5.44 (d, J=3.1 Hz, 1 H, H-4'), 4.91 (dd, 1 H, H-2'), 4.46 (d, J=8.0 Hz, 1 H, H-1'), 3.27 (s, 3 H, OMe), 2.10, 2.03, 2.01 and 1.81 (each s, 12 H, 4×OAc).

Anal Calc. for $C_{44}H_{44}N_2S_{17}$: C, 60.54; H, 5.08; N, 3.21. Found: C, 60.35; H, 5.11; N, 3.16.

Example 4

Preparation of methyl O-(3,4,6-tri-O-acetyl-2-deoxy-2-phthalimido-β-D-galactopyranosyl)-(1→4)-6-O-acetyl-2-deoxy-2-phthalimido-β-D-glucopyranoside (7).—A mixture of compound 6 (1.0 g) and 10% Pd-c (1.0 g) in glacial acetic acid (20 ml) was shaken at ≠345 kPa. The suspension was then filtered (Celite bed), the solids were thoroughly washed with glacial acetic acid, and the combined filtrate and washings were concentrated under reduced pressure. The crude product was applied to a column of silica gel and eluted with hexane-ethyl acetate 2:3→1:4 (v/v). The fractions corresponding to 7 were pooled and concentrated to give an amorphous solid (0.55 g, 62%); $[\alpha]_D$–11° (c 1.5, CHCl$_3$); $^1$H NMR (CDCl$_2$): δ7.89–7.74 (m, 8 H, arom.), 5.79 (dd, 1 H, H-3'), 5.06 (d, J=9.1 Hz, 1 H, H-1), 4.54 (dd, 1 H, H-2'), 3.34 (s, 3 H, OMe), 2.17, 1.91, 1.82 and 1.81 (each s, 12 H, 4×OAc).

Anal Calc. for $C_{37}H_{38}N_2O_{17}$: C, 56.77; H, 4.89; N, 3.58. Found: C, 56.82; H, 4.91; N, 3.49.

Example 5

Preparation of methyl O-(2,3,4-tri-O-2-deoxy-β-D-galactopyranosyl)-(1→4)-O-[2,3,4-tri-O-benzyl-α-L-fucopyranosyl)-(1→3)-O]-6-O-acetyl-2-deoxy-phthalimido-β-D-glucopyranoside (8a).—Glycosidation of 7 (3.9 g, 5.0 mmol) with 3 (10.8 g, 20.0 mmol) in dichloromethane-ether (1:1, 100 ml) and purification of the crude product mixture by silica gel column chromatography [solvent gradient consisting of hexane-ethyl acetate 3:2→1:1 (v/v) furnished compound 8a (3.0 g, 68%); $[\alpha]_D$+ 3° (c 1.5, $CHCl_3$); $^1H$ NMR ($CDCl_2$): δ7.88–6.99 (m, 23 H, arom.), 5.79 (dd, 1 H, H-3'), 5.31 (d, J=4.1 Hz, 1 H, H-1"), 4.89 (d, J=8.6 Hz, 1 H, H-1), 4.82 (d, J=10.0 Hz, 1 H, H-1'), 3.27 (s, 3 H, OMe), 2.07, 2.03, 2.62 and 1.78 (each s, 12 H, 4×OAc), 1.30 (d, J=65. Hz, 3 H, CMe).

Anal Calc. for $C_{64}H_{66}N_2O_{21}$: C, 64.10; H, 5.55; N, 2.34. Found: C, 64.31; H, 5.51; $N_2$, 2.16.

Example 5b

Methyl O-(2-acetamido-2-deoxy-β-D-galactopyranosyl)-(1→4)-O-[α-L-fucopyranosyl)-(1→3)-O]-2-acetamido-2-deoxy-β-D-glucopyranoside (8b)—A mixture of 7 (0.3 g) and 10% Pd-C (0.8 g) in glacial acetic acid (20 ml) was shaken under hydrogen at ≠345 kPa for 16 h at room temperature. After usual workup followed by phthalamido removal with hydrazine hydrate-ethanol (1:4; v/v) at 100° C. for 16 hr and N-acetylation with methanol-triethylamine-acetic anhydride (4:2: 1, v/v) afforded 8b. After purification over a silica gel column with CHCl3-MeOH-water (13:6:1→5:4:1) as the eluent, 8b (0.07 g, 51%); [α]D −88° (c 0.5, H2O); 1H NMR (D2O): δ5.12 (d, J=(s, 3 H, OMe), 2.07 and 2.04 (each s, 6 H, 2×NAc), 1.28 (d, J=6.6 Hz, 3 H, CMe); 13C-NMR: GalNAc-β-(1→4) residue: 100.69 (C-1), 51.34 (C-2), 70.97 (C-3), 66.50 (C-4), 72.36 (C-5), 60.40 (C-6), 21.15 (NAc); Fuc-α-(1→3) residue: 97.41 (C-1), 66.68 (C-2), 68.16 (C-3), 69.79 (C-4), 65.90 (C-5), 14.33 (C-6); GlcNAc-β-OMe residue: 99.72 (C-1), 54.38 (C-2), 74.44 (C-3), 73.81 (C-4), 73.70 (C-5), 59.01 (C-6), 56.09 (OMe), 21.18 (NAc). ES-MS: ml/z=583.22 [M-1]-(584.58).

Anal Calc. for $C_{23}H_{40}N_2O_{15}$: C, 47.25; H, 6.90; N, 4.79. Found: C, 47.09; H, 6.85; N, 4.67.

Example 6

Preparation of O-(3,4,6-tri-O-acetyl-2-deoxy-2-phthalimido-β-D-galactopyranosyl)-(1→4)-O-[(2,3,4-tri-O-acetyl-α-L-fucopyranosyl)-(1→3)-O]-1,6-di-O-acetyl-2-deoxy-2-phthalimido-D-glucopyranose (11).—A solution of compound 8 (6.0 g) in glacial acetic acid (60 ml) was treated with 10% Pd-C (4.0 g) and the mixture was shaken for 16 h at room temperature under hydrogen (≠345 kPa). The suspension was then filtered (Celite bed) and the solids were thoroughly washed with methanol. The filtrate and washings were combined and concentrated and the residue was directly utilized in the next step. A solution of this residue in acetic acid (80 ml) and acetic anhydride (96 ml) containing conc. $H_2SO_4$ (8.4 ml) was stirred for 16 h at 5° C. The mixture was then diluted with dichloromethane (700 ml), and successively washed with water, saturated aqueous sodium bicarbonate solution, water, dried, evaporated to dryness, and redissolved in dichloromethane. Addition of ether-hexane caused the precipitation of 11 as an amorphous solid (4.0 g, 76%); $[\alpha]_D$−63° (c 1.0, $CHCl_3$); $^1H$ NMR ($CDCl_2$): δ7.92–7.78 (m, 8 H, arom.), 6.00 (d, J=8.5 Hz, 0.6 H, H1β), 5.94 (d, J=3.2 Hz, 0.4 H, H-1α), 5.82 (dd, 1H, H-3') 5.51 (d, J=3.8 Hz, 1 H, H-4"), 5.48 (d, J=3.6 Hz, 1 H, H-4'), 5.40 (d, J=4.6 Hz, 1 H, H-1"), 4.83 (d, J=10.6 Hz, 1 H, H-1') 2.22–1.76 (cluster of s, 24 H, 8×OAc), 1.41 (d, J=6.7 Hz, 1.8 H, CMe-β), 1.36 (d, J=6.5 Hz, 1.2 H, CMe-α).

Anal Calc. for $C_{50}H_{54}N_2O_{25}$: C, 55.48; H, 5.03; N, 2.59. Found: C, 55.29; H, 5.11; N, 2.58.

Example 7

Preparation of phenyl O-(3,4,6-tri-O-acetyl-2-deoxy-2-phthalimido-β-D-galactopyranosyl)-(1→4)-O-[(2,3,4-tri-O-acetyl-α-L-fucopyranosyl)-(1→3)-O]-6-O-acetyl-2-deoxy-2-phthalimido-1-thio-α/β-D-glucopyranoside (12).—To a stilled solution of 11 (2.0 6, 1.8 mmol) in dichloromethane (40 ml) was added thiophenol (2.0 ml, 18 mmol) and $BF_3$-ethereate (0.8 ml, 5.6 mmol). Stirring was continued for 5 h at room temperature. The reaction mixture was washed with aqueous sodium bicarbonate solution, water, dried and concentrated. The residue was purified on a column of silica gel with a solvent gradient consisting of hexane-ethyl acetate 1:1→1:4 to afford 12 (1.1 g, 49%); $[\alpha]_D$−72° (c 1.1, $CHCl_3$); $^1HNMR(CDCl_2)$: δ7.91–7.17 (m, 13 H, arom.), 5.84 (dd, 1 H, H-3'), 5.51 (d, J=3.8 Hz, 1 H, H-4"), 5.41 (d, 2.8 Hz, 1H, H-4') 5.36 (d, J=8.4 Hz, 1 H, H-1), 5.34 (d, J=4.0 Hz, 1 H, H-1"), 5.28 (d, J=10.5 Hz, 1 H, H-1'), 5.19 (dd, 1 H, H-2'), 2.20, 2.12, 2.11, 2.08, 2.07, 1.93 and 1.80 (each s, 21 H, 7×OAc), and 1.35 (d, J=6.7 Hz. 3 H, OMe).

Anal Calc. for $C_{54}H_{56}N_2O_{23}$: C, 57.24; H, 4.98; N, 2.47. Found: C, 57.37; H, 5.01; N, 2.29.

Example 8

Methyl O-(2,3,4-tri-O-acetyl-6-O-trimethylacetyl-β-D-galactopyranosyl)-(1→3)-2-acetamido-2-deoxy-α-D-galactopyranoside (9b).—A cold (°C.) and stirred solution of methyl O-(2,3,4-tri-O-acetyl-6-O-trimethylacetyl-β-D-galactopyranosyl)-(1→3)-2-acetamido-2-deoxy-4,6-O-(4-methoxybenzylidene)-α-D-galactopyranoside (9a), in 1:1 dichloromethane-methanol (50 ml) was treated with 0.5 M NaOMe in methanol till the pH was ≠11, and the stirring was continued for 1 h at 0° C. The base was neutralized by string with Amberlite IR-120 ($H^+$) cation-exchange resin, filtered and concentrated. The residue so obtained (≠1.7 g) was taken in N,N-dimethylformamaide (20 ml), sodium bicarbonate (5 g) and chloroacetic anhydride (5.1 g) were then added and the mixture stirred for 16 h at room temperature. It was then poured onto ice-water and stirred. The solid material that separated was filtered, washed with cold water, collected and treated with 70% aqueous acetic acid (100 ml) and stirred for 1 h at 70° C. The mixture was concentrated under diminished pressure and the residue applied to a small column of silica gel and eluted with a solvent gradient consisting of 40–60% acetone in dichloromethane. Fractions corresponding to product were pooled and concentrated and the residue redissolved in dichloromethane. Addition of ether-hexane caused the precipitation of 9b as an amorphous solid (1.8 g, %); $[\alpha]_D$; $^1H$ NMR $^{13}C$ NMR

Example 9

Preparation of Methyl O-(3,4,6-tri-O-acetyl-2-deoxy-2-phthalimido-β-D-galactopyranosyl-(1→4)-O-[(2,3,4-tri-O-acetyl-α-L-fucopyranosyl)-(1→3)-O]-)6-O-acetyl-2-deoxy-2-phthalimido-β-D-glucopyranosyl)-(1→6)-O-[(6-O-trimethylacetyl-β-D-galactopyranosyl)-(1→3)-O]-2-acetamido-2-deoxy-α-D-galactopyranoside (13) and Methyl O-(2-acetamido-2-deoxy-β-D-galactopyranosyl)-(1→4)-O-[(α-L-fucopyranosyl)-(1→3)-O]-(2-acetamido-2-deoxy-β-D-glucopyranosyl)-(1→6)-O-[(β-D-galactopyranosyl)-(1→3)-O]-2-acetamido-2-deoxy-α-D-galactopyranoside (14).—Glycosidation of 9b (0.9 g, 1.26 mmol) with 12 (1.0 g, 0.88 mmol), followed by processing in the usual manner gave a crude product mixture which was directly employed in the next step without further purification. A solution of the crude product in 1:1 ethanol-dichloromethane (30 ml) containing thiourea (2.8 g, 37.8 mmol) and lutidine (2.0 ml, 18.72 mmol) was stirred for 6 h at 80° C. The solvents were evaporated under reduced pressure and the residue redissolved in dichloromethane. The organic layer was washed with water, dried and concentrated under diminished pressure. The residue was purified on a column of silica gel by elution with a solvent gradient consisting of 10–15% MeOH in dichloromethane to give 13 (0.44 g, 37%; based on 12); $[\alpha]_D$ −40° (c 0.5, $CHCl_3$); $^1H$ NMR ($CDCl_2$): δ7.92–7.77 (m, 8 H, arom.), 5.83 (dd, 1 H, H-3'''), 5.76 (d, J=9.6 Hz, 1 H, H-1''), 5.51 (d, J=3.5 Hz, 1H, H-4''''), 5.41 (d, J=2.9 Hz, 1 H, H-4''''), 5.38 (d, J=8.6 Hz, 1 H, H-1'''), 5.22 (d, J=3.3 Hz, 1 H, H-1''''), 5.20 (d, J=2.9 Hz, 1 H, H-1), 2.83 (s, 3 H, OMe), 2.20–1.81, (cluster of s, 24 H, 7×OAc and NAc), 1.36 (d, J=6.4 Hz, 3 H, CMe), and 1.14 (s, 9 H, $CMe_3$).

Anal Calc. for $C_{67}H_{85}N_2O_{35}$: C, 53.92; H, 5.74; N, 2.82. Found: C, 54.03; H, 4.69; N, 2.79.

A portion of compound 13 was treated with hydrazine hydrate in methanol to cleave the phthalimido group, followed by N-acetylation (MeOH-$Et_3N$-$AC_2O$) and finally O-deacetylation in furnish in 66% yield, amorphous 14; $[\alpha]_D$ −12° (c 1.0, $H_2O$); $^1H$ NMR ($D_2O$): δ5.11 (d, J=4.0 Hz, 1 H, H-1''''), 4.74 (d, J=3.8 Hz, 1 H, H-1), 4.52 (d, J=8.3 Hz, 1 H, H-1''), 4.46 (d, J=7.8 Hz, 1 H, H-1'''), 4.44 (d, J 7.0 Hz, 1 H, H-1'), 3.35 (s, 3 H, OMe), 2.04, 2.00 and 1.99 (each s, 9 H, 3×NAc), and 1.26 (d, J=6.6 Hz, 3 H, CMe); $^{13}C$ NMR GalNAc-β-(1→4) residue: 100.36 (C-1), 51.44 (C-2), 69.79 (C-3), 66.76 (C-4), 73.71 (C-5), 60.00 (C-6), 21.23 (NAc); Fuc-α-(1→3): 97.49 (C-1), 67.97 (C-2), 68.24 (C-3), 69.67 (C-4), 65.94 (C-5), 14.40 (C-6); GlcNAc-β-(1→6) residue: 99.76 (C-1), 53.97 (C-2), 74.45 (C-3), 74.00 (C-4), 72.43 (C-5), 59.06 (C-6), 21.30 (NAc); Gal-β-(1→3) residue: 103.68 (C-1), 69.03 (C-2), 71.06 (C-3), 67.63 (C-4), 73.88 (C-5), 60.48 (C-6); GalNAc-α-OMe residue: 97.24 (C-1), 47.56 (C-2), 76.11 (C-3), 66.41 (C-4), 71.58 (C-5), 68.19 (C-6), 54.60 (OMe), 21.06 (NAc). ES-MS: m/z=948.39 [M-1]−.

Anal. Calc. for $C_{37}H_{63}N_2O_{25} \cdot H_2O$: C, 45.91; H, 6.77; N, 4.34. Found: C, 46.08; H, 6.63; N, 4.29.

Example 10

Preparation of methyl O-(3,4,6-tri-O-acetyl-2-deoxy-2-phthalimido-β-D-galactopyranosyl)-(1→4)-O-[(2,3,4-tri-O-acetyl-α-L-fucopyranosyl)-(1→3)-O]-(6-O-acetyl-2-deoxy-2-phthalimido-β-D-glucopylanosyl)-(1→6)-O-[(2,4,6-tri-O-acetyl-3-O-chloroacetyl-β-D-galactopyranosyl-(1→3)-O]-2-acetamido-2-deoxy-α-D-galactopyranoside (17).— Compound 10 (0.92 g, 1.5 mmol) was treated with 12 (1.5 g, 1.3 mmol) as described in the general glycosidation methods. After the customary processing, the crude product was purified by silica gel column chromatography with a solvent gradient consisting of 20–25% acetone in dichloromethane to give 17 (1.0 g, 74%); $[\alpha]_D$ −36° (c 1.0, $CHCl_3$); $^1H$ NMR ($CDCl_2$): δ7.90–7.78 (m, 8 H, arom.), 5.82 (dd, 1 H, H-3'''), 5.50 (d, J=3.5 Hz, 1 H, H-4''''), 5.40 (d, J=3.4 Hz, 1H, H-4''') 5.38 (d, J=7.9 Hz, 1 H, H-1'), 5.21 (d, J=3.5 Hz, 1 H, H-1'''), 5.19 (d, J=3.2 Hz, 1 H, H-1), 5.14 (d, J=8.2 Hz, 1 H, H-1'''), 4.11"4.07 (bs, 2 H, $CH_2Cl$), 2.83 (s, 3 H, OMe), 2.19–1.80 (cluster of s, 3 H, 10×OAc and NHAc), 1.35 (d, J=6.8 Hz, 3 H, CMe).

Example 11

Preparation of methyl O-(3,4,6-tri-O-acetyl-2-deoxy-2-phthalimido-β-D-galactopyranosyl)-(1→4)-O-[(2,3,4-tri-O-acetyl-α-L-fucopyranosyl)-(1→3)-O]-(6-O-acetyl-2-deoxy-2-phthalimido-β-D-glucopyranosyl)-(1→6)-O-[(2,4,6-tri-O-acetyl-β-D-galactopyranosyl)-(1→3)-O]-2-acetamido-2-deoxy-α-D-galactopyranoside (18).—

Compound 17 (0.96 g, 0.58 mmol) was de-O-chloroacetylated in a manner analogous to that described for the preparation of 13 (see Example 8). After customary processing, silica gel column chromatographic purification (5–10% MeOH in dichloromethane), gave 18 (0.65 g, 71%); $[\alpha]_D$ −40° (c 1.0, $CHCl_3$); $^1H$ NMR ($CDCl_2$): δ7.91–7.78 (m, 8 H, arom.), 5.82 (dd, 1 H, H-3'''), 5.50 (d, J=3.7 Hz, 1 H, H-1''''), 5.40 (d, J=3.3 Hz, 1H, H-4''''), 5.38 (d, J=2.9 Hz, 1 H, H-4'''), 5.38 (d, J=9.0 Hz, 1 H, H-1''), 5.25 (d, J=3.5 Hz, 1 H, H-4'), 5.23 (d, J=3.4 Hz, 1 H, H-1'''), 5.19 (d, 2.9 Hz, 1 H, H-1), 2.81 (s, 3 H, OMe), 2.20–1.58, (cluster of s, 33 H, 10×OAc and NHAc), 1.35 (d, J=6.2 Hz, 3 H, CMe).

Anal Calc. for $C_{72}H_{89}N_3O_{37}$: C, 54.44; H, 5.65; N, 2.64. Found: C, 54.19; H, 5.73; N, 2.59.

Example 12

Preparation of methyl O-(3,4,6-tri-O-acetyl-2-deoxy-2-phthalimido-β-D-galactopyranosyl)-(1→4)-O-[(2,3,4-tri-O-acetyl-α-L-fucopyranosyl)-(1→3)-O]-6-O-acetyl-2-deoxy-2-phthalimido-β-D-glucopyranosyl)-(1→6)-O-[methyl-(5-acetamido-4,7,8,9-tetra-O-acetyl-3,5-dideoxy-D-glycero-α-D-galacto-2-nonulopyranosylonate-(2→3)-O-(6-O-trimethylacetyl-β-D-galactopyranosyl-(1→3)-O]-2-acetamido-2-deoxy-α-D-galactopyranoside (15).— Compound 13 (0.2 g, 0.13 mmol) was treated with donor 4 (0.6 g, 1.1 mmol) in propionitile (15 ml) at −65° C. for 3 h. The reaction mixture was then processed as described in the general methods, and the crude product subjected to column chromatography on silica gel with 10% MeOH in dichloromethane as the eluent to give 15 (0.12 g, 46%); $[\alpha]_D$ −28° (c 0.5, $CHCl_3$); $^1H$ NMR ($CDCl_2$): δ7.88–7.76 (m, 8 H, arom.), 5.48 (d, J=9.2 Hz; 1 H, NH), 5.84 (dd, 1 H, H-3'''), 5.49 (d, J=3.3 Hz, 1H, H-4''''), 5.40 (d, J=3.0 Hz, 1 H, H-4''''), 5.37 (d, J=8.6 Hz, 1 H, H-1''), 5.28 (d, J=3.3 Hz, 1 H, H-1''''), 5.18 (d, J=3.3 Hz, 1 H, H-1), 5.14 (d, J=9.4 Hz, 1 H, H-1'''), 3.78 (s, 3 H, OMe), 2.79 (s, 3 H, OMe), 2.67 (dd, J=4.6 Hz, H-3e'''''), 2.18–1.77, (cluster of s, 39 H, 12×OAc and NHAc), 1.34 (d, J=6.5 Hz, 3 H, CMe) and 1.15 (s, 9 H, $CMe_3$).

Anal Calc. for $C_{87}H_{112}N_4O_{47}$: C, 53.15; H, 5.74; N, 2.85. Found: C, 53.09; H, 5.89; N, 2.93.

Example 13

Preparation of methyl O-(2-acetamido-2-deoxy-β-D-galactopyranosyl-(1→3)-O]-(2-acetamido-2-deoxy-β-D-glucopyranosyl)-(1→6)-O-[(5-acetamido-3,5-dideoxy-D-glycero-α-D-galacto-2-nonulopyranosylonic acid)-(2→3)-O-(β-D-galactopyranosyl)-(1→3)-O]-2-acetamido-2-deoxy-α-D-galactopyranoside (16).—A solution of 15 (0.1 g, 0.05 mmol) and lithium iodide (0.3 g, 2.2 mmol) in pyridine (10 ml) was stirred for 6 h at ≠120° C. The solvent was then removed under diminished pressure and the residue was passed through a small column of silica gel by elution with 20–30% methanol in dichloromethane to give the protected free acid derivative. This compound was taken in methanol-hydrazine hydrate (4:1, 20 ml) and heated at ≠80° C. for 16 h. After evaporation to dryness, the residue was redissolved in methanol-dichloromethane (1:1, 20 ml) and treated with acetic anhydride (6 ml) for 1 h at 0° C. The mixture was then evaporated to dryness and the residue so obtained was deacetylated by stilling in methanolic sodium methoxide (20 ml) for 2 days at room temperature. The crude product was purified by column chromatography on silica gel by using chloroform-methanol-water 13:6:1 and 4:5:1 (v/v/v) as the eluent, to give the target compound 16 (0.015 g, 24%); [α]$_D$ −8° (c 0.15, H$_2$O); $^1$H NMR (D$_2$O): δ5.11 (d, J=3.9 Hz, 1 H, H-1''''), 4.76 (d, J=3.9 Hz; 1 H, H-1), 4.52 (d, J=8.2 Hz, 1 H, H-1''), 4.51 (d, J=7.7 Hz, 1H, H-1'''), 4.46 (d, J=7.0 Hz, 1 H, H-1'), 3.34 (s, 3 H, OMe), 2.75 (dd, J$_{3''''e,4''''}$=4.6 Hz, 1 H, H-3''''e), 2.04, 2.03, 2.01 and 1.99 (each s, 12 H, 4×NHAc), 1.81 (t, J$_{3''''a,4''''}$=J3''''a, 3''''e=12.1 Hz, 1 H, H-3''''a), and 1.26 (d, J=6.5 Hz, 3 H, CMe); $^{13}$C NMR; D20; GalNAc-β-(1→4) residue: 100.36 (C-1), 51.43 (C-2), 69.79 (C-3), 66.77 (C-4), 73.72 (C-5), 60.00 (C-6), 21.23 (Nac); Fuc-α-(1→3) residue: 97.49 (C-1), 67.83 (C-2), 68.24 (C-3), 69.12 (C-4), 65.94 (C-5), 14.41 (C-6); GlcNAc-β-(1→6) residue: 99.76 (C-1), 53.97 (C-2), 74.44 (C-3), 73.87 (C-4), 72.44 (C-5), 59.05 (C-6), 21.30 (NAc); Gal-β-(1→3) residue: 103.46 (C-1), 68.22 (C-2), 76.22 (C-3), 66.42 (C-4), 73.81 (C-5), 60.49 (C-6); NeuAc-α-(2→3) residue: 174.05 (C-1), 98.75 (C-2), 38.82 (C-3), 67.16 (C-4), 50.73 (C-5), 71.85 (C-6), 67.40 (C-7), 70.86 (C-8), 61.59 (C-9), 21.12 (NAc); GalNAc-α-OMe residue: 97.21 (C-1), 47.46 (C-2), 74.71 (C-3), 66.42 (C-4), 71.07 (C-5), 68.09 (C-6), 54.62 (OMe), 21.09 (NAc). ES-MS: m/z=1239.8 [M−1]-.

Anal Calc. for C$_{48}$H$_{80}$N$_4$O$_{33}$·1.5 H$_2$O: C, 45.46; H, 6.60; N, 4.42. Found: C, 45.37; H, 6.62; N, 4.40.

Example 14

Preparation of methyl O-(2-acetamido-2-deoxy-β-D-galactopyranosyl-(1→4)-O-[α-L-fucopyranosyl-(1→3)-O]-(2-acetamido-2-deoxy-β-D-glucopyranosyl)-(1→6)-O-[(3-O-sulfo-β-D-galactopyranosyl sodium salt)-(1→3)-O]-2-acetamido-2-deoxy-α-D-galactopyranoside (19).—
Compound 18 (0.45 g, 0.29 mmol) in N,N-dimethylformamide (20 ml) was treated with sulfur trioxide-pyridine complex (0.25 g, 1.6 mmol) at 0° C. for 5 h. Excess reagent was destroyed by the addition of methanol (≠5 ml), followed by pyridine (≠5 ml). The mixture was then concentrated under diminished pressure and the residue was passed through a small column of silica gel by using 15–20% methanol in dichloromethane as the eluent. The fractions corresponding to product were pooled and concentrated and the residue taken in methanol-hydrazine hydrate (4:1, 50 ml) and heated at ≠90 C. for 5 h. The mixture was then concentrated and the crude product mixture was taken in methanol-triethylamine (2:1, 25 ml), cooled (0° C.) and treated with acetic anhydride (5 ml). It was allowed to gradually attain room temperature and kept for an additional 1 h at same temperature. The mixture was concentrated, and the residue applied to a column of silica gel and eluted with chloroform-methanol-water 13:6:1 and 4:5:1 (v/v/v). Fractions corresponding to product were pooled and concentrated and the residue redissolved in water and passed through a small column of Amberlite IR-120 (Na$^+$) cation exchange resin. Lyophilization of the eluate then furnished 19 (0.11 g, 37%), [α]$_D$ (c 1.0, H$_2$O); $^1$H NMR (D$_2$O): δ5.12 (d, J=3.9 Hz, 1 H, H-1''''), 4.77 (d, J=3.7 Hz; 1 H, H-1), 4.57 (d, J=7.9 Hz, 1 H, H-1''), 4.54 (d, J=8.3 Hz, 1H, H-1'''), 4.48 (d, J=8.2 Hz, 1 H, H-1'), 3.37 (s, 3 H, OMe), 2.07, 2.03 and 2.02 (each s, 9 H, 3×NAc), and 1.27 (d, J=6.6 Hz, 3 H, CMe); $^{13}$C NMR (D2O); GalNAc-β-(1→4) residue: 100.37 (C-1), 51.44 (C-2), 69.79 (C-3), 66.77 (C-4), 73.57 (C-5), 59.90 (C-6), 21.14 (NAc); Fuc-α-(1→3) residue: 97.50 (C-1), 67.76 (C-2), 68.24 (C-3), 69.11 (C-4), 65.85 (C-5), 14.41 (C-6); GlcNAc-β-(1→6) residue: 99.76 (C-1), 53.99 (C-2), 74.45 (C-3), 73.88 (C-4), 72.44 (C-5), 59.06 (C-6), 21.31 (NAc); 3-O-SO3Na Gal-β-(1→3) residue: 103.37 (C-1), 68.21 (C-2), 79.29 (C-3), 66.42 (C-4), 73.73 (C-5), 60.48 (C-6); GalNAc-α-OMe residue: 97.25 (C-1), 47.48 (C-2), 76.55 (C-3), 65.40 (C-4), 71.07 (C-5), 67.87 (C-6), 54.62 (OMe), 21.06 (NAc). ES-MS: m/z=1028.38 [M−Na]-.

Anal Calc. for C$_{37}$H$_{62}$N$_3$O$_{28}$·SNa. 2 H$_2$O: C, 40.84; H, 6.11; N, 3.86. Found: C, 40.73; H, 6.15; N, 3.73.

Inhibition Studies Data

Relative Inhibitory Properties of Branched Chains Including Neu5Ac and/or GalNAcLe$^x$ Against Recombinant Selectins Binding to Immobilized SLe$^x$

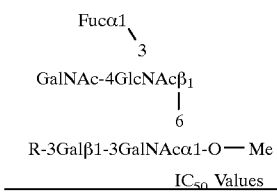

R-3Galβ1-3GalNAcα1-O—Me

| | | IC$_{50}$ Values | | |
| | | (μM) Against SLe$^x$ | | |
| Compound | R | E-Selectin | P-Selectin | L-Selectin |
| --- | --- | --- | --- | --- |
| 14 | OH | >500 | 400 μM | 300 μM |
| 16 | Neu5Ac | >500** | 85 μM | 105 μM |
| 19 | 3-SE | >500 μM | >500 | 500 μM |
| 8b | | >500 | 400 | 300 |
| sialyl Lewis$^x$ | | 540 | 520 | 600 |

ELISA inhibition studies were done as previously reported conditions. Ic$_{50}$ values against immobilized SLe$^x$ are the mean values of 3 determinations and were calculated according to published methodology.

This clearly shows that compound 19 has about six times the binding ability of sialyl Lewis$^x$ for P-selectin. Other studies show even greater binding for compound 19.

To the best of our knowledge, structures 14, 16 and 19 have not been reported to be part of any glycoproteins. Our findings are the first to clearly demonstrate the role of the NeuAc2→3Gal β1→3galNAc chain of core 2 structures in binding with L and P selectins.

What is claimed is:

1. A compound having the structure

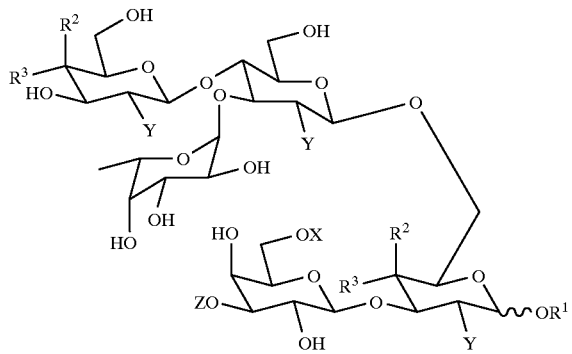

wherein R$^1$ is independently H, alkyl, aryl, an aryl alkyl, alkenyl or one or more additional saccharide residues;

R$^2$=H or OH provided that when R$^2$ is H, R$^3$ is OH;

R$^3$=H or OH provided that when R$^3$ is H, R$^2$ is OH,

X=H, SO$_3$— or PO$_4$—;

Y is independently H, OH, OR$^4$ or NHCOR$^4$, wherein R$^4$ is alkyl;

Z is an organic acid residue; and wherein the hydroxy groups of the fucose moiety can be substituted independently at each occurrence H or $OR^5$ where $R^5$ is a methyl, ethyl or allyl group.

2. The compound of claim 1 which is methyl O-(2-acetamido-2-deoxy-β-D-galactopyranosyl)-(1→4)-O-[(α-L-fucopyranosyl)-(1→3)-O]-(2-acetamido-2-deoxy-β-D-glucopyranosyl)-(1→6)-O-[(β-D-galactopyranosyl)-(1→3)-O]-2-acetamido-2-deoxy-α-D-galactopyranoside.

3. The compound of claim 1 which is methyl O-(2-acetamido-2-deoxy-β-D-galactopyranosyl)-(1→3)-O]-(2-acetamido-2-deoxy-β-D-glucopyranosyl)-(1→6)-O-[(5-acetamido-3,5-dideoxy-D-glycero-α-D-galacto-2-nonulopyranosylonic acid)-(2→3)-O-(β-D-galactopyranosyl)-(1→3)-O]-2-acetamido-2-deoxy-α-D-galactopyranoside.

4. The compound of claim 1 which is methyl O-(2-acetamido-2-deoxy-β-D-galactopyranosyl)-(1→4)-O-[α-L-fucopyranosyl-(1→3)-O]-(2-acetamido-2-deoxy-β-D-glucopyranosyl)-(1→6)-O-[(3-O-sulfo-β-D-galactopyranosyl sodium salt)-(1→3)-O]-2-acetamido-2-deoxy-α-D-galactopyranoside.

5. The compound of claim 1 in a pharmaceutical carrier.
6. The compound of claim 2 in a pharmaceutical carrier.
7. The compound of claim 3 in a pharmaceutical carrier.
8. The compound of claim 4 in a pharmaceutical carrier.

* * * * *

UNITED STATES PATENT AND TRADEMARK OFFICE
CERTIFICATE OF CORRECTION

PATENT NO. : 5,972,907
DATED : October 26, 1999
INVENTOR(S) : Khushi L. Matta, et al.

It is certified that error appears in the above-identified patent and that said Letters Patent is hereby corrected as shown below:

Column 1, after the title, insert --This work is sponsored by the National Institute of Health Grant Nos. CA 35329 and CA 63218. The U.S. Government may have certain rights in this invention. --

Column 15, line 10, after the word "galactopyranosyl-" insert -- (1→4)-O-[(α-L-fucopyranosyl)- --.

In Claim 1, penultimate line, change "H" to -- with -H --

Signed and Sealed this

Twentieth Day of June, 2000

Attest:

Q. TODD DICKINSON

Attesting Officer

Director of Patents and Trademarks